United States Patent

Goodyear et al.

[11] Patent Number: 6,051,709
[45] Date of Patent: Apr. 18, 2000

[54] PROCESS FOR THE DIASTEREOSELECTIVE SYNTHESIS OF NUCLEOSIDE ANALOGUES

[75] Inventors: Michael David Goodyear; P. Owen Dwyer; Malcolm Leithead Hill; Andrew Jonathan Whitehead, all of Stevenage; Roy Hornby, Buntingford; Peter Hallett, Royston, all of United Kingdom

[73] Assignee: Glaxo Group Limited, Greenford, United Kingdom

[21] Appl. No.: 08/722,224

[22] PCT Filed: Apr. 21, 1995

[86] PCT No.: PCT/EP95/01503

§ 371 Date: Dec. 24, 1996

§ 102(e) Date: Dec. 24, 1996

[87] PCT Pub. No.: WO95/29174

PCT Pub. Date: Nov. 2, 1995

[30] Foreign Application Priority Data

Apr. 23, 1994 [GB] United Kingdom .................. 9408091
Apr. 23, 1994 [GB] United Kingdom .................. 9408103
Apr. 23, 1994 [GB] United Kingdom .................. 9408112

[51] Int. Cl.[7] ...................... C07D 407/04; C07D 409/04; C07D 411/04
[52] U.S. Cl. ........................... 544/314; 544/318; 544/317
[58] Field of Search ................................. 544/317, 314, 544/318

[56] References Cited

U.S. PATENT DOCUMENTS 5,047,407  9/1991  Belleau et al. ........................ 544/274
5,210,085  5/1993  Liotta et al. ............................ 544/317
5,466,806  11/1995 Belleau et al. ........................ 544/310
5,486,520  1/1996  Belleau et al. ........................ 514/274
5,532,246  7/1996  Belleau et al. ........................ 514/274
5,538,975  7/1996  Dionne .................................. 514/256
5,539,116  7/1996  Liotta et al. ............................ 544/317
5,587,480  12/1996 Belleau et al. ........................ 544/310
5,618,820  4/1997  Dionne .................................. 514/274
5,684,164  11/1997 Belleau et al. ........................... 549/30

FOREIGN PATENT DOCUMENTS 0 515 157  11/1992  European Pat. Off. .
91 17159  11/1991  WIPO .
94 14802   7/1994  WIPO .

OTHER PUBLICATIONS

Chang, C.-N. et al. *J. Biol. Chem.*, vol. 267, pp. 13938–13942 (1992).

*Primary Examiner*—John M. Ford
*Attorney, Agent, or Firm*—Bacon & Thomas

[57] ABSTRACT

The invention relates to a diastereoselective process for the preparation of compounds of formula (I), wherein W is S, S=O, $SO_2$ or O; X is S, S=O, $SO_2$ or O; $R_1$ is hydrogen or acyl, and $R_2$ is a purine or pyrimidine base or an analogue or derivative thereof.

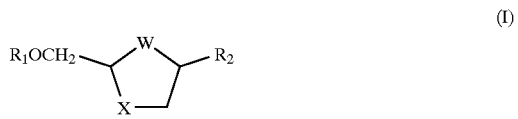

(I)

14 Claims, No Drawings

PROCESS FOR THE DIASTEREOSELECTIVE SYNTHESIS OF NUCLEOSIDE ANALOGUES

The present invention relates to a diastereoselective process for the preparation of optically active cis-nucleoside analogues and derivatives.

Nucleosides and their analogues and derivatives are an important class of therapeutic agents. For example, a number of nucleoside analogues have shown antiviral activity against retroviruses such as human immunodeficiency virus (HIV), hepatitis B virus (HBV) and human T-lymphotropic virus (HTLV) (PCT publication WO 89/04662 and European Patent publication 0349242 A2).

In particular, 4-Amino-1-(2R-hydroxymethyl-[1,3] oxathiolan-5S-yl)-1H-pyrimidin-2-one, which may be represented by the following formula:

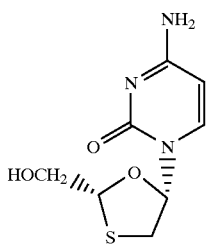

(also known as 3TC™ or lamivudine) and its pharmaceutically acceptable derivatives, disclosed in International application PCT/GB91/00706, publication no. WO91/17159, has been described as having antiviral activity, in particular against retroviruses such as the human immunodeficiency viruses (HIV's), the causative agents of AIDS (WO91/17159) and hepatitis B virus (HBV) (European Patent Application Publication no. 0474119).

Most nucleosides and nucleoside analogues and derivatives contain at least two chiral centres (shown as * in formula (A)), and exist in the form of two pairs of optical isomers (i.e., two in the cis-configuration and two in the trans-configuration). However, generally only the cis-isomers exhibit useful biological activity. Therefore a general stereoselective synthesis of cis nucleoside analogues is an important goal.

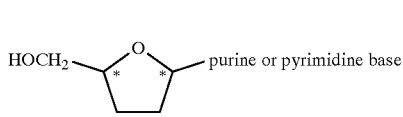

(A)

Different enantiomeric forms of the same cis-nucleoside analogue may, however, have very different antiviral activities. M M Mansuri et al., "Preparation of The Geometric Isomers of DDC, DDA, D4C and D4T As Potential Anti-HIV Agents", *Bioorg. Med. Chem. Lett.*, 1 (1), pp. 65–68 (1991). Therefore, a general and economically attractive stereoselective synthesis of the enantiomers of the biologically active cis-nucleoside analogues is an important goal.

International patent application publication no. WO92/20669 discloses a diastereoselective process for producing optically active cis-nucleoside analogues and derivatives of formula (I).

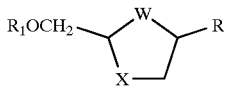

(I)

wherein
W is S, S=O, SO$_2$, or O;
X is S, S=O, SO$_2$ or O;
R$_1$ is hydrogen or acyl; and
R$_2$ is a desired purine or pyrimidine base or an analogue or derivative thereof;
the process comprising the step of reacting the desired purine or pyrimidine base or analogue thereof with an intermediate of formula (IIa) or (IIb)

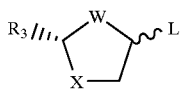

(IIa)

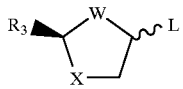

(IIb)

wherein
R$_3$ is a substituted carbonyl or carbonyl derivative; and
L is a leaving group;
using a Lewis acid of the formula (III)

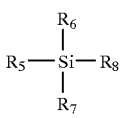

(III)

wherein
R$_5$, R$_6$ and R$_7$ are independently selected from the group consisting of hydrogen; C$_{1-20}$ alkyl optionally substituted by fluoro, bromo, chloro, iodo, C$_{1-6}$ alkoxy or C$_{6-20}$ aryloxy; C$_{7-20}$ aralkyl optionally substituted by halogen, C$_{1-20}$ alkyl or C$_{1-20}$ alkoxy C$_{6-20}$ aryl optionally substituted by fluoro, bromo, chloro, iodo, C$_{1-20}$ alkyl or C$_{1-20}$ alkoxy; trialkylsilyl; fluoro; bromo; chloro and iodo; and
R$_8$ is selected from the group consisting of fluoro; bromo; chloro; iodo; C$_{1-20}$ sulphonate esters, optionally substituted by fluoro, bromo, chloro or iodo; C$_{1-20}$ alkyl esters optionally substituted by fluoro, bromo, chloro or iodo, polyvalent halides; trisubstituted silyl groups of the general formula (R$_5$) (R$_6$) (R$_7$) Si (wherein R$_5$, R$_6$, and R$_7$ are as defined above); saturated or unsaturated selenenyl C$_{6-20}$ aryl; substituted or unsubstituted C$_{6-20}$ arylsulphenyl; substituted or unsubstituted C$_{6-20}$ alkoxyalkyl; and trialkylsiloxy.

The process of WO92/20669 allows the stereo-controlled synthesis of a racemic cis-nucleoside analogue from an equimolar mixture of (IIa) and (IIb), and of a given enantiomer of a desired cis-nucleoside analogue in high optical purity if the starting material is optically pure (IIa) or (IIb). However, the WO92/20669 process relies on the use of a Lewis acid of formula (III).

There are a number of disadvantages associated with the use of such Lewis acids. In particular, they are highly reactive and unstable compounds and there are therefore hazards associated with their use. Furthermore, they are expensive and have significant toxic effects. These disadvantages are of particular importance in relation to the large-scale production of nucleoside analogues in factory processes.

We have now found that, by judicious selection of the leaving group L in intermediates (IIa) and (IIb), the reaction with the purine or pyrimidine base, or analogue thereof, can be successfully effected without the addition of a Lewis acid catalyst, and in particular, without the addition of a Lewis acid of formula (III).

The present invention accordingly provides a stereoselective process for producing cis-nucleoside analogues and derivatives of formula (I)

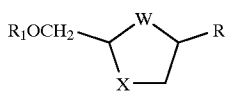

(I)

wherein

W is S, S=O, SO$_2$, or O;

X is S, S=O, SO$_2$, or O;

R$_1$ is hydrogen or acyl; and

R$_2$ is a purine or pyrimidine base or an analogue thereof;

the process comprising the step of glycosylating the purine or pyrimidine base or analogue or derivative thereof with an intermediate of formula (IVa) or (IVb)

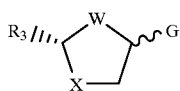

(IVa)

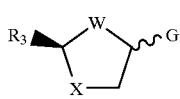

(IVb)

wherein R$_3$ is a substituted carbonyl or carbonyl derivative; and

G represents halo, cyano or R$^9$SO$_2$- where R$^9$ represents alkyl optionally substituted by one or more halo, or optionally substituted phenyl;

characterised in that the glycosylation reaction is effected without the addition of a Lewis acid catalyst.

In a preferred embodiment, the present invention provides a stereoselective process for producing cis-nucleoside analogues and derivatives of formula (I) as previously defined, which process comprises the step of glycosylating the purine or pyrimidine base or analogue or derivative thereof with an intermediate of formula (IVa) or (IVb) as previously defined, characterised in that the glycosylation reaction is effected without the addition of a Lewis acid of formula (III):

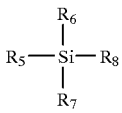

(III)

wherein

R$_5$, R$_6$ and R$_7$ are independently selected from the group consisting of hydrogen; C$_{1-20}$ alkyl optionally substituted by fluoro, bromo, chloro, iodo, C$_{1-6}$ alkoxy or C$_{6-20}$ aryloxy; C$_{7-20}$ aralkyl optionally substituted by halogen, C$_{1-20}$ alkyl or C$_{1-20}$ alkoxy; C$_{6-20}$ aryl optionally substituted by fluoro, bromo, chloro, iodo, C$_{1-20}$ alkyl or C$_{1-20}$ alkoxy; trialkylsilyl; fluoro; bromo; chloro and iodo; and R$_8$ is selected from the group consisting of fluoro; bromo; chloro; iodo; C$_{1-20}$ sulphonate esters, optionally substituted by fluoro, bromo, chloro or iodo; C$_{1-20}$ alkyl esters optionally substituted by fluoro, bromo, chloro or iodo, polyvalent halides; trisubstituted silyl groups of the general formula (R$_5$) (R$_6$) (R$_7$) Si (wherein R$_5$, R$_6$, and R$_7$ are as defined above); saturated or unsaturated selenenyl C$_{6-20}$ aryl; substituted or unsubstituted C$_{6-20}$ arylsulphenyl; substituted or unsubstituted C$_{6-20}$ alkoxyalkyl; and trialkylsiloxy.

It will be appreciated that, if the glycosylation step is carried out using an equimolar mixture of intermediates (IVa) and (IVb), a racemic mixture of cis-nucleoside analogues will be obtained. However, it is preferred that glycosylation is effected using an optically pure compound of formula (IVa) or (IVb), thereby producing the desired cis-nucleoside analogue in high optical purity.

A "nucleoside" is defined as any compound which consists of a purine or pyrimidine base linked to a pentose sugar.

As used herein, a "nucleoside analogue or derivative" is a compound containing a 1,3-oxathiolane, 1,3-dioxolane or 1,3-dithiolane linked to a purine or pyrimidine base or an analogue thereof which may be modified in any of the following or combinations of the following ways: base modifications, such as addition of a substituent (e.g., 5-fluorocytosine) or replacement of one group by an isosteric group (e.g., 7-deazaadenine); sugar modifications, such as substitution of hydroxyl groups by any substituent or alteration of the site of attachment of the sugar to the base (e.g., pyrimidine bases usually attached to the sugar at the N-1 site may be, for example, attached at the N-3 or C-6 site and purines usually attached at the N-9 site may be, for example, attached at N-7).

A purine or pyrimidine base means a purine or pyrimidine base found in naturally occurring nucleosides. An analogue thereof is a base which mimics such naturally occurring bases in that its structure (the kinds of atoms and their arrangement) is similar to the naturally occurring bases but may either possess additional or lack certain of the functional properties of the naturally occurring bases. Such analogues include those derived by replacement of a CH moiety by a nitrogen atom, (e.g., 5-azapyrimidines such as 5-azacytosine) or conversely (e.g., 7-deazapurines, such as 7-deazaadenine or 7-deazaguanine) or both (e.g., 7-deaza, 8-azapurines). By derivatives of such bases or analogues are meant those bases wherein ring substituents are either incorporated, removed, or modified by conventional substituents known in the art, e.g., halogen, hydroxyl, amino, C$_{1-6}$ alkyl. Such purine or pyrimidine bases, analogues and derivatives are well known to those skilled in the art.

As used herein, halo means bromo, chloro, fluoro or iodo.

As used herein, unless otherwise stated, alkyl means straight, branched or cyclic saturated hydrocarbon groups, or mixtures thereof.

Optionally substituted phenyl means unsubstituted phenyl or phenyl substituted by one or more $C_{1-6}$alkyl, nitro, amino, halo or cyano groups.

Preferably $R_2$ is a pyrimidine base. More preferably $R_2$ is cytosine or 5-fluorocytosine.

$R_3$ is a carbonyl linked to hydrogen, hydroxyl, trialkylsilyl, trialkylsiloxy, $C_{1-30}$ alkyl, $C_{7-30}$ aralkyl, $C_{1-30}$ alkoxy, $C_{1-30}$ alkylamine (secondary or tertiary), $C_{1-30}$ alkylthio; $C_{6-20}$ aryl; $C_{2-20}$ alkenyl; $C_{2-20}$ alkynyl; or $R^3$ is 1,2-dicarbonyl, such as

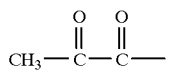

optionally substituted with $C_{1-6}$ alkyl or $C_{6-20}$ aryl; or $R^3$ is an anhydride, such as

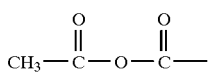

optionally substituted with $C_{1-6}$ alkyl or $C_{6-20}$ aryl; or $R^3$ is an azomethine linked at nitrogen to hydrogen, $C_{1-20}$ alkyl or $C_{1-10}$ alkoxy or $C_{1-20}$ dialkylamino and at carbon to hydrogen, $C_{1-20}$ alkyl, or $C_{1-20}$ alkoxy;
or $R^3$ is a thiocarbonyl (C=S) substituted with hydroxyl, $C_{1-20}$ alkoxy, or $C_{1-20}$ thiol.

Preferably $R_3$ represents a group —C(=O)OR$_4$ where $R_4$ represents an optionally substituted alkyl group. Preferably $R_4$ represents a chiral auxiliary.

The term "chiral auxiliary" describes an asymmetric molecule that is used to effect the chemical resolution of a racemic mixture. Such chiral auxiliaries may possess one chiral centre such as α-methylbenzylamine or several chiral centres such as menthol. The purpose of the chiral auxiliary, once built-into the starting material, is to allow simple separation of the resulting diastereomeric mixture. See, for example, J Jacques et al., *Enantiomers, Racemates and Resolutions*, pp. 251–369, John Wiley & Sons, New York (1981).

Preferably the chiral auxiliary $R_4$ will be selected from (d)-menthyl, (l)-menthyl, (d)-8-phenylmenthyl, (l)-8-phenylmenthyl, (+)-norephedrine and (−)-norephedrine. More preferably $R^4$ is (l)-menthyl, or (d)-menthyl, most preferably (l)-menthyl.

Preferably W is O.

Preferably X is S.

Preferably G represents halo such as Cl, Br or I, more preferably Cl,

The intermediates of formulae (IVa) and (IVb) may be isolated or they may conveniently be generated in situ.

Suitably the intermediates of formulae (IVa) and (IVb) are generated from the corresponding trans alcohols of formulae (Va) and (Vb):

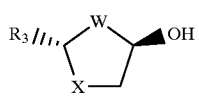

(Va)

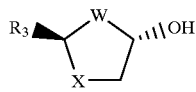

(Vb)

wherein $R_3$, W and X are as previously defined, or from the epimeric cis alcohols of formulae (Vc) and (Vd):

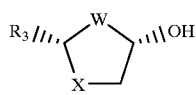

(Vc)

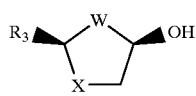

(Vd)

by reaction with a reagent, suitable to introduce the group G.

Suitable reagents for introducing the group G will be readily apparent to those skilled in the art and include halogenating agents such as, for example oxalyl bromide. Preferred halogenating agents are Vilsmeier-type reagents, which may conveniently be generated in situ by reaction of an N,N-disubstituted amide, such as dimethylformamide (DMF), and a halogenating agent such as an oxalyl halide, e.g. oxalyl chloride, a thionyl halide, e.g. thionyl chloride, a phosphorus halide, e.g. phosphorus trichloride or phosphorus oxychloride, an alkyl or phenyl sulphonyl halide or anhydride. The halogenation reaction is suitably effected under conventional conditions.

The intermediate of formula (IVa) or (IVb) is reacted with a silylated purine or pyrimidine base, conveniently in a suitable organic solvent such as a hydrocarbon, for example, toluene, a halogenated hydrocarbon such as dichloromethane, a nitrile, such as acetonitrile, an amide such as dimethylformamide, an ester, such as ethyl acetate, an ether such as tetrahydrofuran, or a ketone such as acetone, or a mixture thereof, preferably at elevated temperature, such as the reflux temperature of the chosen solvent.

Silylated purine and pyrimidine bases may be prepared as described in WO92/20669, the teaching of which is incorporated herein by reference, for example by reacting the purine or pyrimidine base with a silylating agent such as t-butyidimethylsilyl triflate, 1, 1, 1, 3, 3, 3-hexamethyldisilazane, trimethylsilyl triflate or trimethylsilyl chloride, with acid or base catalyst, as appropriate. Suitable methods are described in detail in the accompanying examples.

The cis-nucleoside analogue obtained from the reaction of the compound of formulas (Va) and (Vb) with the purine or pyrimidine base or analogue thereof may then be reduced to give a specific stereoisomer of formula (I). Appropriate reducing agents will be readily apparent to those skilled in the art and include, for example, hydride reducing agents such as lithium aluminium hydride, lithium borohydride or sodium borohydride. We have found that stereointegrity is maintained using sodium borohydride in the presence of a phosphate or borate buffer, for example dipotassium hydrogen phosphate, as the reducing agent.

According to the process of the invention, as well as the process described in WO92/20669, the final compound is typically obtained as a solution in a polar solvent, such as an aqueous solvent. This presents a practical problem in that compounds of formula (I) have a high solubility in polar media, making their efficient isolation from such media difficult. We have now found that compounds of formula (I) may be efficiently isolated from solution in polar solvents by formation of a salt having poor aqueous solubility. If desired, the water-insoluble salt may subsequently be converted to the free base, or to a different salt thereof by conventional methods. We have further found that the salicylate salt is particularly suitable for this purpose.

The present invention thus provides a process as previously described further comprising the step of isolating the compound of formula (I) as a water-insoluble salt, especially a salicylate salt.

Salicylate salts of compounds of formula (I) are within the scope of the pharmaceutically acceptable derivatives described and claimed in European Patent Application publication no. 0382526 and publication no. WO91/17159, but are not specifically disclosed therein. Such salts are therefore novel and form a further aspect of the present invention.

In a further or alternative aspect, the present invention provides salicylate salts of compounds of formula (I), or hydrates thereof.

In particular, we have found that formation of the salicylate salt of 4-amino-1-(2R-hydroxymethyl-[1,3]oxathiolan-5S-yl)-1H-pyrimidin-2-one (lamivudine, 3TC™) affords considerable advantages for the isolation of that compound from polar solvents.

In a preferred embodiment the invention therefore provides 4-amino-1-(2R-hydroxymethyl-[1,3]oxathiolan-5S-yl)-1H-pyrimidin-2-one salicylate, or hydrates thereof.

The salicylate salt of lamivudine is a pharmaceutically acceptable salt and as such it and its hydrates may be used as antiviral agents as described in WO91/17159, which is incorporated herein by reference.

The salicylate salt of lamivudine or its hydrates may be formulated as a pharmaceutical composition as described in WO91/17159.

The salicylate salts of compounds of formula (I) may be prepared by treating a solution containing a compound of formula (I) with salicylic acid. Suitable solvents include for example, water and polar organic solvents such as ethers, for example tetrahydrofuran or dioxan and alcohols, for example methanol and ethanol, or mixtures of solvents, in particular mixtures containing an organic solvent and water.

The salicylate salts are conveniently converted, if desired, to the corresponding free bases by treatment with a base, suitably a tertiary amine such as, for example triethylamine.

Other suitable water-insoluble salts and methods for their preparation and conversion to free bases will be readily appreciated by those skilled in the art.

Intermediate alcohols (Va) and (Vb) and the epimeric cis alcohols (Vc) and (Vd) may be prepared by the methods described in WO92/20669, for example, by reduction of the corresponding carbonyl compounds or by condensation of an aldehyde of formula $R_3$-CHO, or a derivative thereof, with hydroxyacetaldehyde or mercaptoacetaldehyde, or suitable derivatives thereof. Further details of the preparation of such alcohols may be found in the accompanying examples.

Compounds of formulae (Va) and (Vb) are key intermediates for the preparation of enantiomerically pure cis-nucleoside analogues or derivatives, according to the process of the invention. The absolute stereochemistry of the groups $R_3$, W and X in (Va) or (Vb) is preserved in the resulting cis-nucleoside analogue or derivative of formula (I).

Reactions for the preparation of alcohols of formulae (Va) and (Vb) and their cis epimers (Vc) and (Vd) typically result in the formation of mixtures of isomers. When compounds of formulae (Va) or (Vb) are isolated by crystallisation from mixtures containing their enantiomers and/or their cis stereoisomers, the yield may be limited by the proportion of the desired isomer (Va) or (Vb) present in solution.

We have now found that crystallisation of the trans isomers (Va) and (Vb) is favoured over the crystallisation of the corresponding cis isomers (Vc) and (Vd). Where $R_3$ is an achiral moiety, a 1:1 mixture of the trans isomers (Va) and (Vb) may be crystallised from mixtures of the cis and trans isomers (Va), (Vb), (Vc) and (Vd).

Accordingly, the present invention provides, in a further or alternative aspect, a method for enhancing the yield of the trans isomers (Va) and (Vb) from a mixture of the trans and cis isomers, which method comprises treatment of the mixture of trans and cis isomers, at least partially in solution, with an agent capable of effecting interconversion of the isomers without complete suppression of the crystallisation of the trans isomers.

We have further discovered that, where $R_3$ is a chiral moiety, a single trans enantiomer of formula (Va) or (Vb) may be selectively crystallised from a mixture of stereoisomers.

Thus, for example, compounds of formula (Va) wherein $R_3$ represents —C(=O)$R_4$, where $R_4$ is l-menthyl, can be selectively crystallised from a mixture of stereoisomers, in particular a mixture containing alcohols (Va), (Vb) and the epimeric cis alcohols (Vc) and (Vd).

Similarly, compounds of formula (Vb) wherein $R_3$ represents —C(=O)$R_4$, where $R_4$ is d-menthyl, can be selectively crystallised from a mixture of stereoisomers, in particular a mixture containing alcohols (Va), (Vb) and the epimeric cis alcohols (Vc) and (Vd).

Therefore, in a preferred aspect, the present invention provides a method for enhancing the yield of a single enantiomer of formula (Va) or (Vb) from a mixture of isomers, which method comprises treatment of the mixture of isomers, at least partially in solution, with an agent capable of effecting interconversion of the isomers without complete suppression of the crystallisation of the desired single enantiomer (Va) or (Vb).

Agents capable of effecting interconversion of the isomers without complete suppression of the crystallisation of the trans isomers include, for example, alcohols, such as, for example, methanol, ethanol, n-propanol, i-propanol, n-butanol, i-butanol, t-butanol, and organic bases, in particular tertiary amines, for example, pyridine and triethylamine and Hunig's base. A preferred agent is triethylamine.

The interconversion of isomers may be effected in any suitable solvent or mixture of solvents which does not otherwise react with the alcohols of formulae (Va) or (Vb) or their cis isomers, under conditions of concentration and temperature which permit crystallisation of the desired isomer or isomers and which do not cause significant degradation of the desired isomer or isomers. Suitable solvents may include for example, aliphatic or aromatic hydrocarbons, ethers, esters and chlorinated hydrocarbons. The interconversion will preferably be effected at a temperature of about −20° to 120° C., more preferably in the range of about −10° to 80° C., such as about 0° to 50° C.

It will be appreciated by those skilled in the art that selection of solvent, temperature, interconversion agent and, particularly, the quantity of the interconversion agent is best conducted as an integrated exercise dependent on the nature of the groups $R_3$, X and W present in the isomers. However, when an organic base is used as the interconversion agent, the preferred quantity is generally less than two mole-equivalents based on the total of all isomers of (Va) and (Vb) present.

Further guidance as to preferred reaction conditions may be gained from the accompanying examples.

The interconversion of isomers may be conducted separately from the preparation of the isomeric mixture; however, it is conveniently conducted concomitantly with that preparation.

The interconversion procedure may also be used to increase the isomeric purity of isolated (Va) or (Vb).

By means of the interconversion process, the isolated yield of the desired isomer (Va) or (Vb) may be enhanced to greater than 50% of theory (based on formation of all stereoisomers), typically to between about 60% and about 90% of theory; but it is not ruled out that yields approaching 100% of theory may be obtained.

A particularly preferred embodiment of the process of the present invention using l-menthol as chiral auxiliary is represented in Scheme 1 and is described in detail in the accompanying examples, which are to be construed as illustrative of the invention and not as limiting thereof.

Scheme 1

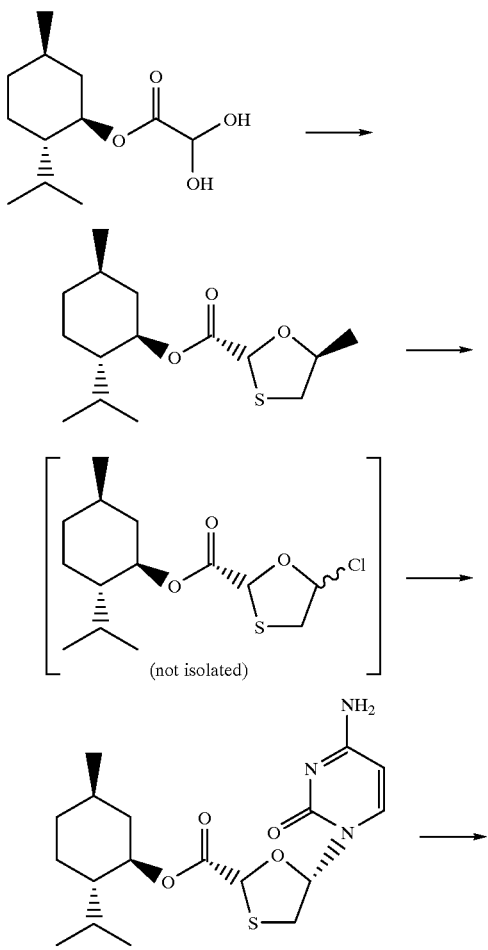

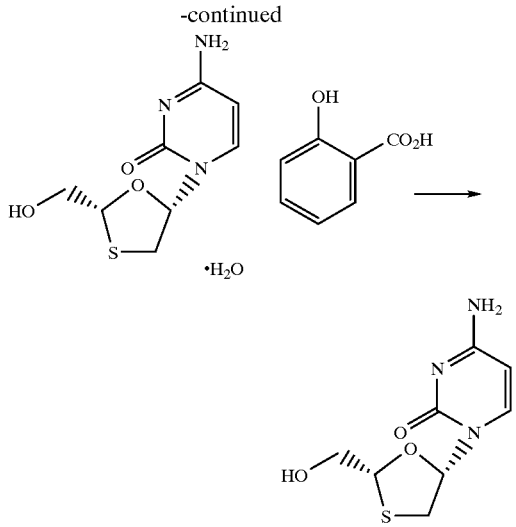

The invention is further illustrated by the following non-limiting examples. All temperatures are in degrees centigrade. DMSO means dimethyl sulphoxide.

EXAMPLE 1

4-Amino-1-(2R-hydroxymethyl-[1,3]oxathiolan-5S-yl)-1H-pyrimidin-2-one (a) (2R,5R)-5-Hydroxy-[1,3]oxathiolane-2-carboxylic acid, 2S-isopropyl-5R-methyl-1R-cyclohexyl ester.

A mixture of l-menthyl glyoxylate hydrate (25 g) and acetic acid (2.5 mL) in toluene (125 mL) was stirred and heated to reflux. Water was removed by azeotropic distillation via a Dean-Stark trap. The resulting solution of l-menthyl glyoxylate was concentrated by distillation under reduced pressure collecting ca 70 mL distillate, and then cooled to 20–25°. The volume was adjusted to 75 mL by adding ca 15 mL toluene, dithianediol (8.25 g) was added, and the mixture heated at reflux for about 1 h. The mixture was cooled to about 80°, and clarified. The filtrate was cooled to 0–5°, and a solution of triethylamine (1.5 mL) in hexane (150 mL) was added over ca 1.25 h at 0–5°. The resulting suspension was stirred at 0–5° for about 6 h, then the product isolated by filtration. The product was washed with a mixture of toluene and hexane (1:3, 2×50 mL), and dried in vacuo at 40–45° to constant weight.

(b) (2R,5R)-5-(4-Amino-2-oxo-2H-pyrimidin-1-yl)-[1,3]oxathiolane-2-carboxylic acid, 2S-isopropyl-5R-methyl-1R-cyclohexyl ester A solution of (2R,5S)-5-chloro-[1,3]oxathiolane-2-carboxylic acid, 2S-isopropyl-5R-methyl-1R-cyclohexyl ester was prepared as follows:

A solution of (2R,5R)-5-hydroxy-[1,3]oxathiolane-2-carboxylic acid, 2S-isopropyl-5R-methyl-1R-cyclohexyl ester (300 g) in dichloromethane (3000 mL) containing methanesulphonic acid (0.7 mL) was treated with dimethylformamide (85 mL), cooled to ca 8° and thionyl chloride (80 mL) added over ca 10 min. The resultant solution was stirred at 10–15° for ca 1.5 h, then concentrated by distillation under atmospheric pressure (over ca 1.5 h), collecting ca 2.1 L distillate. The solution was cooled to 20–25°.

A solution of silylcytosine was prepared as follows:

A suspension of cytosine (115.5 g), methanesulphonic acid (0.7 mL) and hexamethyldisilazane (242 mL) was heated in toluene (290 mL) at reflux until a clear solution was obtained (ca 1.5 h).

The solution of silylcytosine was treated with triethylamine (145 mL), the solution of (2R,5S)-5-chloro-[1,3]oxathiolane-2-carboxylic acid, 2S-isopropyl-5R-methyl-1R-cyclohexyl ester added maintaining a gentle reflux, washing in with dichloromethane (300 mL). The resulting mixture was heated at reflux for 4 h, and added to a mixture of triethylamine (73 mL) and water (1200 mL) held at 30–35°, over ca 1.5 h. The resulting suspension was stirred for ca 45 min, then hexane (1200 mL) added over ca 10 min at 30–35°. The suspension was stirred at ambient temperature overnight, then filtered. The solid was washed with water (2×600 mL) and isopropyl acetate (2×600 mL), and dried in vacuo at 40–45° to constant weight. $^1$HNMR (D$_6$-DMSO) $\delta_H$ 0.75 (3H,d); 0.89(d), 0.9(m), 0.91(d), 1.0–1.2(m) (9H); (9H,m); 1.43, 1.50 (2H,m); 1.67 (2H,m); 1.9–2.0 (2H,m); 3.14 (1H,dd); 3.55 (1H,dd); 4.69 (1H,dt); 5.70 (1H,s); 5.80 (1H,d), 6.36 (1H,dd), 7.28 (brs), 7.33 (brs) (2H); 7.97 (1H,d).

(c) 4-Amino-1-(2R-hydroxymethyl-[1,3]oxathiolan-5S-yl)-1H-pyrimidin-2-one monosalicylate A solution of dipotassium hydrogen phosphate (137 g) in water (150 mL) was stirred at ca 20°, and (2R,5R)-5-(4-amino-2-oxo-2H-pyrimidin-1-yl)-[1,3]oxathiolane-2-carboxylic acid, 2S-isopropyl-5R-methyl-1R-cyclohexyl ester (100 g) added. IMS (750 mL) was added, and the suspension stirred for 10 min. A solution of sodium borohydride (20 g) in water (200 mL) containing sodium hydroxide solution, 25% w/w (2 mL) was added over 70 min, keeping the temperature in the range 15–30°. The addition funnel was rinsed with water (50 mL), and the mixture stirred at 15–30° until the reaction was judged complete by HPLC (150 min). The mixture was allowed to settle, and the lower aqueous layer discarded. The pH of the organic phase remaining was adjusted to 4–4.5 with conc. hydrochloric acid (27 mL), whilst maintaining the temperature in the range 20–25°. The addition funnel was rinsed with water (20 mL), then the pH of the solution adjusted to 6.8–7.2 with 2M sodium hydroxide solution (110 mL). The addition funnel was rinsed with water (20 mL), and the reaction mixture was transferred to a distillation vessel, washed in with water (50 mL), and the solution heated to reflux. The solution was concentrated to ca 6.45 vol under atmospheric pressure, then cooled to 20–25°.

Menthol was removed by extraction with toluene (500 mL, 2×200 mL), the aqueous phase was diluted with water (255 mL) then treated with salicylic acid (36 g), washing in with water (40 mL). The mixture was heated to give a solution (at 71°), then cooled to 58°. The solution was seeded with authentic lamivudine salicylate, then cooled to 5–10° over ca 4 h. The suspension was stirred for 1 h at this temperature, then filtered. The product was washed with water (1×100 mL, 2×200 mL), and dried in vacuo at 45–50° to constant weight. $^1$HNMR (D$_6$-DMSO) $\delta_H$ 3.11 (dd), 3.45 (dd) (2H); 3.77 (2H,m); 5.20 (1H,m); 5.82 (1H,d); 6.22 (1H,m); 6.91 (2H,m); 7.48 (1H,m); 7.62 (2H,br); 7.80 (1H,dd); 7.92 (1H,d).

(d) 4-Amino-1-(2R-hydroxymethyl-[1,3]oxathiolan-5S-yl)-1H-pyrimidin-2-one

4-Amino-1-(2R-hydroxymethyl-[1,3]oxathiolan-5S-yl)-1H-pyrimidin-2-one monosalicylate (66.7 g) was stirred with IMS (470 mL), and heated to 70–75° to give a solution. The solution was clarified into a crystallisation vessel, and rinsed in with a further 170 mL IMS. Triethylamine (26 mL) was added, and the solution distilled until 280 mL remained. The solution was cooled to 70° over 20 min, seeded, then isopropyl acetate held at 60° (600 mL) added over 2.25 h, maintaining the temperature above 55°. The mixture was cooled to room temperature overnight, then cooled to 8–10° and stirred for 1 h. The product was isolated by filtration (transferred to the filter with 30 mL isopropyl acetate), washed with isopropyl acetate (2×130) and dried in vacuo at 40–45°, to constant weight. $^1$HNMR (D$_6$-DMSO) $\delta_H$ 3.10 (1H,dd); 3.39 (1H,dd); 3.72 (2H,m); 5.15 (1H,t); 5.29 (1H, t); 5.72 (1H,d); 6.19 (1H,dd); 7.17 (1H, brs); 7.22 (1H,brs); 7.80 (1H,d).

We claim:

1. In a stereoselective process for producing cis nucleosides of formula (I)

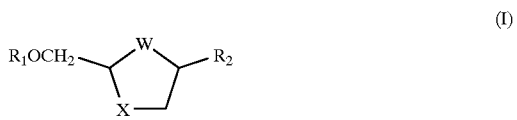

wherein

W is S, S=O, SO$_2$, or O;

X is S, S=O, SO$_2$, or O;

R$_1$ is hydrogen or acyl; and

R$_2$ is a pyrimidine base or an analogue or a derivative thereof, which comprises the step of reacting the pyrimidine base or an analogue or derivative thereof with an intermediate compound in the presence of a Lewis acid catalyst; said intermediate compound being selected from the group consisting of formulae (IIa) and (IIb):

wherein W and X are as defined in formula (I), R$_3$ is a substituted carbonyl or carbonyl derivative, and L represents a leaving group;

wherein the improvement comprises limiting said leaving group to halo, cyano or R$^9$SO$_2$- wherein R$^9$ represents alkyl optionally substituted by one or more halo, or optionally substituted phenyl; and said step of reacting the pyrimidine base or analogue or derivative thereof with said intermediate compound is effected without the Lewis acid catalyst.

2. A process as claimed in claim 1 which further includes production of the intermediates of formulae (IIa) and (IIb) wherein said intermediates are produced from the corresponding trans alcohols of formulae (Va) and (Vb).

3. A process as claimed in claim 1 further comprising the step of reducing R$_3$ to the group R$_1$OCH$_2$.

4. A process as claimed in claim 3 wherein the reduction is effected using sodium borohydride in the presence of a borate or phosphate buffer.

5. A process as claimed in claim 1 wherein R$_2$ is a pyrimidine base.

6. A process as claimed in claim 5 wherein R$_2$ is cytosine or 5-fluorocytosine.

7. A process as claimed in claim 1 wherein R$_3$ represents a group —C(=O)OR$_4$ where R$_4$ represents an optionally substituted alkyl group.

8. A process as claimed in claim 7 wherein $R_4$ represents a chiral auxiliary.

9. A process as claimed in claim 8 wherein $R_4$ is selected from (d)-menthyl, (l)-menthyl, (d)-8-phenylmenthyl, (l)-8-phenylmenthyl, (+)-norephedrine and (−)-norephedrine.

10. A process as claimed in claim 1 wherein W is O and X is S.

11. A process as claimed in claim 1 wherein L represents Cl, Br or I.

12. A process as claimed in claim 1 wherein the compound of formula (I) is isolated as a water-insoluble salt.

13. A process as claimed in claim 1 wherein the compound of formula (I) is 4-amino-1-(2R-hydroxymethyl-oxathiolan-5S-yl)-1H-pyrimidin-2-one or a salicylate salt thereof.

14. A process as claimed in claim 2 wherein the intermediates of formulae (IIa) and (IIb) are generated in situ.

* * * * *